United States Patent [19]
Francis et al.

[11] Patent Number: 4,923,876
[45] Date of Patent: May 8, 1990

[54] VINCA ALKALOID PHARMACEUTICAL COMPOSITIONS

[75] Inventors: Daniel L. Francis, Albuquerque, N. Mex.; Robert Kasubick, Auora, Ohio

[73] Assignee: Cetus Corporation, Emeryville, Calif.

[21] Appl. No.: 204,391

[22] Filed: Jun. 9, 1988

Related U.S. Application Data

[63] Continuation-in-part of Ser. No. 185,231, Apr. 18, 1988, abandoned, which is a continuation of Ser. No. 83,507, Aug. 7, 1987, abandoned, which is a continuation of Ser. No. 918,387, Oct. 14, 1986, abandoned.

[51] Int. Cl.$^5$ .............................................. A61K 31/44
[52] U.S. Cl. ................................................... 514/283
[58] Field of Search ................................. 514/283, 281

[56] References Cited

U.S. PATENT DOCUMENTS

| | | | |
|---|---|---|---|
| 3,097,137 | 5/1960 | Beer et al. | 514/281 |
| 3,205,220 | 9/1985 | Svoboda et al. | 514/281 |
| 4,203,898 | 5/1980 | Cullinan et al. | 514/281 |
| 4,259,242 | 3/1981 | Rolski | 514/281 |
| 4,619,935 | 10/1986 | Robison | 514/281 |

FOREIGN PATENT DOCUMENTS

| | | | |
|---|---|---|---|
| 553514 | 7/1986 | Australia . | |
| 3324964 | 1/1984 | Fed. Rep. of Germany | 514/283 |
| 835081 | 7/1983 | South Africa . | |
| 2125292 | 6/1986 | United Kingdom . | |

OTHER PUBLICATIONS

Chen, J. R., 1982, Abstracts, 12:41.

Primary Examiner—Jerome D. Goldberg
Attorney, Agent, or Firm—Philip L. McGarrigle; Albert P. Halluin

[57] ABSTRACT

Disclosed herein are ready-to-use solutions comprising pharmaceutical compositions suitable for intravenous injection which are stable at room temperature. Pharmaceutical formulations of this invention comprise aqueous compositions of a pharmaceutically-acceptable vinca dimer salt, a citrate buffer and a preservative, wherein the composition pH is between 3.0 and 5.0.

8 Claims, No Drawings

VINCA ALKALOID PHARMACEUTICAL COMPOSITIONS

BACKGROUND OF RELATED APPLICATIONS

This application is a continuation-in-part of of copending U.S. Ser. No. 185,231 filed Apr. 18, 1988, now abandoned which is a continuation of U.S. Ser. No. 083,507, filed Aug. 7, 1987, now abandoned, which is a continuation of U.S. Ser. No. 918,387, filed Oct. 14, 1986, now abandoned.

FIELD OF THE INVENTION

This invention is in the field of pharmaceutical compositions. More particularly, the invention concerns improved pharmaceutical compositions of vinca alkaloids which are stable at room temperature and are suitble for therapeutic administration to humans.

BACKGROUND OF THE INVENTION

The vinca alkaloids are, in general, dimeric indoledihydroindole compounds. Two of the vinca alkaloids, vincristine and vinblastine, are obtained from the leaves of the plant *Vinca rosea* L. (Apocynaceae) and are marketed for the treatment of leukemias and related neoplasms in humans.

Specifically, vincristine, the chemical name for which is 22-oxovincaleukoblastine, is an antineoplastic, especially used in the treatment of acute leukemia. ($C_{46}H_{58}N_4O_9$)

Vinblastine, the chemical name for which is vincaleukoblastine, is an antineoplastic employed in the palliative treatment of lymphomas, including generalized Hodgkin's disease, lymphosarcoma, reticulum-cell sarcoma, and advanced mycosis fungoides, and of neuroblastoma, Letterer-Siwe disease, choriocarcinoma resistent to other agents, breast carcinoma resistant to other agents, and embryonal carcinoma of the testes. ($C_{46}H_{58}N_4O_9$)

A third vinca alkaloid is vindesine, an amide derivative of vinblastine, the chemical name for which is 23-amino-$O^4$-deacetyl-23-demethoxyvincaleukoblastine, is another antineoplastic. ($C_{43}H_{55}N_5O_7$)

Vincristine, vinblastine and vindesine are described respectively in U.S. Pat. No. 3,205,220; 3,097,137; and 4,203,898. The three drugs are administered intravenously to patients suffering from susceptible neoplasms.

Standard pharmaceutical formulations of the three vinca alkaloids are lyophilized vials of the sulfate salt thereof which are reconstituted prior to use. The sulfate salts are prepared by adding the theoretical amount of sulfuric acid to a solution of the alkaloidal free base. However, in the case of vindesine, the sulfate thereof made by such procedure is not stable, and is prepared according to a procedure described in U.S. Pat. No. 4,259,242 for the lyophilized pharmaceutical formulation.

South African Patent No. 835,081 outlines the problem related to such lyophilized pharmaceutical formulations requiring reconstitution for administration, and points out the need for stable, ready-to-use solutions of vincristine sulfate and other vinca alkaloids. The problems with the lyophilized formulations mainly revolve around the extreme potency of the oncolytic, cytostatic drugs. Because of their cytostatic activity, minimizing contact with the drugs by hospital personnel and accurately calculating and administering dosages are pharmaceutical concerns of great importance. Improper reconstitution of the lyophilized formulations can create air-borne droplets hazardous to hospital personnel. Errors in calculating the quantity of diluent can result in accidental overdosages as the margin between toxic and therapeutic dosages are very small with the vinca alkaloids. See, for example, *J. Pediatrics* 89: 671 (1976); *Cancer Chemotherapy Rept.*, 55: 525 (1972 and *J. Pediatrics* 90: 1041 (1977).

Further, the vinca alkaloids are very expensive, for example, vincristine sulfate is approximately $2000 per gram. As the lyophilized formulations of vincristine sulfate are supplied in whole milligram amounts, for example, 1 mg or 5 mg vials, whereas the dosages are actually given in decimal milligram amounts (2 mg per square meter of body surface for children and 1.4 mg per square meter of body surface for adults), only part of a vial's contents may be used for a single patient. As the recommended life for reconstituted vincristine is 14 days at refrigerated temperatures, unless the treatment facility employing the drug is a large cancer treatment center with many patients, waste of the vinca alkaloid occurs when it is necessary to discard excess reconstituted lyophilized solution that has outlasted the 14-day period.

Upon standing, the physical changes noticed for reconstituted lyophilized vincristine (reconstituted with 0.9% aqueous sodium chloride containing benzyl alcohol as a preservative) are a general haziness of solution followed by the appearance of a precipitate.

Another problem associated with reconstituted vincristine formulations is the need to incorporate a preservative in order to prevent the growth of microorganisms. Although vincristine solutions cannot generally be heat sterilized, they can be sterilized by filtration, but even if so sterilized, a preservative must be present in the diluent used to reconstitute the lyophilized material in an opened, previously sterilized liquid vial because of the possibility of contamination from the air. If it were not for the preservatives, the excess material would have to be discarded immediately and could not even be kept for the recommended maximum 14-day period.

Reconstituted solutions of vinblastine sulfate and vindesine sulfate have similar problems associated with the vincristine sulfate reconstituted solutions. However, since both vinblastine and vindesine sulfate contain an N-methyl group instead of the more labile N-formyl functionality of vincristine, stability problems thereof are not as pronounced and the recommended reconstituted stability period is for 30 rather than 14 days.

Formulations of the invention are also applicable to other vinca dimers including 4'-deoxy-1-formylleurosidine sulfate and leuroformine. The stabilized formulations of the invention are especially useful with the N-formyl vinca dimers such as vincristine or 4'-deoxy-1-formylleurosidine because they decompose by an additional mechanism, that is, by the loss of the N-formyl group, which is not a problem with the methyl containing vinblastine or vindesine.

Therefore, for the reasons outlined above, stable, ready-to-use solutions of the vinca alkaloids are required by both considerations for safety and economy. South African Patent No. 835,081 discloses aqueous pharmaceutical formulations which comprise a pharmaceutically-acceptable vinca dimer salt, a polyol, and acetate buffer, which maintains the pH of the solution between 3.0 and 5.0, and a preservative as useful, stable oncolytic preparations. Such a ready-to-use solution minimizes the contact between hospital personnel and the drug and provides a single solution strength for all the syringe sizes employed, thereby avoiding errors during reconstitution and in calculation of dosage amounts.

The present invention provides ready-to-use solutions of vinca alkaloids which are stable at room temperature and contain a citratephosphate buffer.

SUMMARY OF THE INVENTION

The pharmaceutical formulations of this invention comprise compositions of a pharmaceutically-acceptable vinca dimer salt selected from the group consisting essentially of vincristine, vinblastine, 4'-deoxy-1-formylleurosidine or leuroformine, a citrate-buffer, and a preservative selected from the group consisting of benzyl alcohol, phenol, m-cresol and methyl and/or propyl paraben or mixtures thereof, wherein the pH of the solution is between 3.0 and 5.0. The formulations of this invention provide ready-to-use solutions of oncolytic vinca alkaloids for intravenous injection which are stable at room temperature. Preferably, the vinca dimer salt is vincristine sulfate.

Among other factors, it has been surprisingly discovered that the incorporation of a citrate buffer provides an unexpectedly stable formulation.

A more specific formulation comprises a pharmaceutical formulation comprising per ml of a final solution about 1 mg of vincristine sulfate, 1-2 mg of a preservative selected from methyl paraben and propyl paraben either alone or in combination, and water for injection in a quantity sufficient to provide 1 ml with a pH of said solution between about 4.4-4.8 maintained by a 0.002-0.01M citrate buffer.

The vinca alkaloids that can be formulated according to this invention include but are not limited to: vincristine sulfate, vinblastine sulfate, vindesine sulfate, 4'-deoxyl-1-formylleurosidine and leuroformine. Pharmaceutically-acceptable salts, other than the sulfate salts, such as the phosphate salt, may be used in the stable solutions of this inventtion, although the sulfate salts are preferred. Pharmaceutically-acceptable salts are those salts useful in the chemotherapy of warm-blooded animals.

The vinca alkaloids are present in the formulations of this invention at concentrations of about 0.01 to 2.5 mg/ml, preferably at a concentration of about 0.1 to about 1.5 mg/ml.

The ready-to-use solutions stable at room temperature of oncolytic vinca dimers of this invention can optionally include a polyol, although the preferred formulation will not include one. If included, the preferred polyols employed in the formulations of this invention are selected from the group comprising sorbitol, inositol, galactitol, xylitol, mannitol, lactose and dextrose. Mannitol is particularly preferred. Such polyols are usually present in the formulation at a concentration from about 10-300 mg/ml, preferably 75-125 mg/ml.

The buffer system utilized in the solution of this invention preferably maintains the pH in the range of 3.0-6.0. The preferred pH ranges vary with the individual vinca alkaloid that is being stabilized in solution. In the case of vincristine sulfate, a pH range of 4-5 is preferred and more preferably a pH range of 4.4-4.8. For vinblastine sulfate, the preferred pH range is lower than for vincristine sulfate and is in the range of 3.5-4.5, preferably 3.8-4.2. For vindesine sulfate, a further lower pH range is preferred, preferably in the range of 3.0-4.0 and more preferably in the range of 3.0-3.6.

Preferably the buffer system comprises citrate, although a citrate phosphate buffer can also be used. Citrate is especially preferred as the buffer system because it can maintain the stability of the drug formulations for an unexpectedly long time. This is especially true for vincristine. Sodium hydroxide is preferably added to the citrate to adjust the pH.

The molarity range for the buffer system is from about 0.0005 to about 0.02M, preferably from about 0.002 to about 0.01M. The molar ratio of buffer to the vinca dimer is preferably about 20 to 1 or less. In the case of vindesine sulfate, at pHs below 3.6, the buffer consists only of citric acid and no citrate-phosphate salt is employed.

Formulations of this invention further comprise a preservative. Such preservative can include benzyl alcohol, preferably in a weight to volume concentration from about 0.5% to about 1.5%,, preferably 0.75 to 1.25%, and most preferably about 0.945%. The preservatives also include phenol, m-cresol and the parabens, methyl and propyl. Preferably, the preservatives of the formulations of this invention are methyl and propyl parabens which can be used singly or in combination, preferably in a total amount of 0.5-3 mg/ml, and more preferably, 1-2 mg/ml. The liquid formulations of this invention are sterilized preferably by filtration.

As chloride ions are known to have a deleterious effect on the various oncolytic vinca dimers, it is preferred that the chloride ion concentrations be minimized in formulating the compositions of this invention.

The following examples further illustrate the formulations of the instant invention. These examples are not intended to limit the invention in any manner.

EXAMPLE 1

A ready-to-use solution of vincristine sulfate that is stable at room temperature was prepared according to the following procedure. Citric acid (26.7 ml of 0.1M) was added to dibasic sodium phosphate (23.3 ml of 0.2M), and the solution was diluted to 100ml with water for injection (WFI) with a resulting pH of 4.58.

Methyl paraben (39 mg) and propyl paraben (6 mg) were added to 15 ml of the citrate-phosphate buffer solution. The mixture was heated to 50° C. to dissolve the parabens. Within approximately 10 minutes, a clear, colorless solution was effected.

Ten ml of citrate-phosphate was added to the paraben solution, and mixing was continued. The solution was allowed to cool to approximately 22° C. Mannitol (3.0 gm) was slowly added to the solution over a period of about 20 minutes.

Vincristine sulfate (30 mg; crystalline powder from Omnichem) was added to the cooled paraben/buffer solution, and dissolved therein with mixing for about three minutes. A clear, colorless solution at about 20° C. and at pH 4.58 resulted.

A quantity of citrate-phosphate buffer sufficient to expand the volume to 30 ml was added, and the solution was mixed for about five minutes.

The solution was then filtered through a Pall NR 0.2 micron membrane. The solution filtered easily at 40 psi. The filtrate was a very clear, colorless solution.

EXAMPLE 2

The stability at room temperature of the vincristine sulfate formulation of Example 1 was tested by employing high pressure liquid chromatography (HPLC) analysis. Room temperature in this example is considered to be between 15° C. and 30° C., inclusive. The room temperature samples were maintained in a room monitored to prevent the temperature from rising above or falling below said temperature range. However, the average temperature of the room wherein the samples were stored was considered to remain at or about 20° C. Therefore, the text of this sample refers to said room temperature samples as being stored at about 20° C.

Samples of the bulk solution prepared according to Example 1 were maintained in amber, sulfate treated, tubing vials with 1888 Teflon ® laminated plug closures at 50° C., 20° C. and 5° C., respectively. (Teflon ® is the registered trademark of E. I. duPont de Nemours & Co., Inc. for polytetrafluoroetylene resins and products.) Forty-eight hours after preparation, a 5 ml sample of the solution maintained at 50° C. was analyzed by HPLC and compared to an HPLC chromatogram of a 5-ml sample of a freshly prepared solution. The freshly prepared standard solution was formulated according to the procedure of Example 1 and comprised 5 mmg of vincristine sulfate, 6.5 mg of methyl paraben, 1.0 mg of propyl paraben and 500 mg of mannitol in 5 ml of citratephosphate buffer pH 4.58). The HPLC chromatograms indicated that at 48 hours after preparation, the formulation maintained at 50° C. showed a peak representing vincristine sulfate that was 98.52% of the area of the standard's peak for vincristine sulfate.

The HPLC testing routine, exemplified immediately above, was then performed at 7-day intervals over a 12-week period on samples of the representative formulation of this invention stored at 50° C. and about 20° C., respectively., and on freshly prepared samples. The chromatograms were then compared. Table I, below, shows the results of the periodic HPLC testing throughout the 12-week period. The percentages listed represent the area for vincristine sulfate on an HPLC chromatogram of the stored samples as a percentage of the corresponding area on the HPLC chromatograms of the standard formulations prepared at the time of testing, which latter area is considered to represent theoretically 100% of the vincristine sulfate originally present in the formulations.

TABLE I

| | Sample | |
|---|---|---|
| Days after preparation | Bulk solution maintained at 50° C. | Bulk solution maintained at room temperature |
| 2 | 98.52% | — |
| 7 | 94.9% | 99.2% |
| 14 | 88.9% | 98.3% |
| 28 | 61.4% | 98.4% |
| 42 | 44.7% | 97.2% |
| 56 | 28.1% | 100.2% |
| 70 | — | 98.1% |
| 84 | — | 97.4% |

It can be seen from the results in Table I that the representative formulation of this invention maintained at room temperature remained stable throughout the test period whereas the formulation heated to 50° C. began to lose stability within the second week and within the fourth to seventh weeks of the study the vincristine sulfate therein had decomposed. The results therefore indicate that the formulation representative of those of this invention is stable at room temperature for at least 12 weeks.

EXAMPLE 3

Preparation of Formulation with Citrate

A ready to use solution of vincristine sulfate, that is stable at room temperature, was prepared according to the following procedure. Methyl paraben (130 mg) and propyl paraben (20 mg) were added to approximately 80 ml of Water for Injection (WFI). The mixture was heated to 50° C. to dissolve the parabens. Within approximately 10 minutes a clear, colorless solution was effected. The solution was cooled to approximately 22° C.

Mannitol (10 g) was slowly added to the solution over a period of 20 minutes.

Vincristine sulfate (100 mg) was added to the solution. Citric acid (190 mg) was added with a resulting pH of approximately 2.

Sufficient sodium hydroxide (0.1M) was added with stirring to produce a pH of 4.5. A quantity of WFI was added to expand the volume to 100 ml, and the solution was mixed for about five minutes.

The solution was then filtered through a Pall NR 0.2 micron membrane filter. The solution filtered easily at 40 psi. The filtrate was a clear, colorless, solution.

EXAMPLE 4

Preparation of Formulation with Acetate

A ready to use solution of vincristine sulfate was prepared according to the following procedure. Methyl paraben (130 mg) and propyl paraben (20 mg) ware added to approximately 80 ml of Water for Injection (WFI). The mixture was heated to 50° C. to dissolve the parabens. Within approximately 10 minutes a clear, colorless solution was effected. The solution was cooled to approximately 22° C.

Mannitol (10 g) was slowly added to the solution over a period of 20 minutes.

Vincristine sulfate (100 mg) was added to the solution. Acetic acid (600 mg) and sodium acetate (460 mg) were added with a resulting pH of approximately 4.4.

A quantity of WFI was added to expand the volume to 100 ml, and the solution was mixed for about five minutes The solution was then filtered through a Pall NR 0.2 micron membrane filter. The solution filtered easily at 40 psi. The filtrate was a clear, colorless solution.

EXAMPLE 5

Comparison of Formulations

The formulations of Example 3 (citrate) and Example 4 (acetate) are compared in the table below.

| Ingredient | Acetate* | Citrate* |
|---|---|---|
| Vincristine | 1.0 mg | 1.0 mg |
| Mannitol | 100.0 | 100.0 |
| Methyl paraben | 1.3 | 1.3 |
| Propyl paraben | 0.2 | 0.2 |
| Acetic acid | 6.0 | — |
| Sodium acetate | 4.6 | — |
| Citric acid | — | 1.9 |
| Sodium hydroxide | — | q.s. to pH 4.5 |
| Water for Injection | q.s. to 1.0 | |

*concentrations given in mg/ml.

Samples of the above formulations were taken according to the following schedule.

| Temperature | Time | | |
|---|---|---|---|
| 5° C. | 1 month | 2 months | 3 months |
| 25° C. | 0.5 month | 1 month | |
| 35° C. | 0.5 month | 1 month | |

The samples were assayed for the decomposition compound N-desformyl vincristine, the total related substances, and the percent highest individual impurity. The results are given in the tables below.

TABLE II

Percent N-Desformyl Vincristine as a Stability Measurement

| Time | 5° C. | | 25° C. | | 35° C. | |
|---|---|---|---|---|---|---|
| | acetate | citrate | acetate | citrate | acetate | citrate |
| 0 | 0.84% | 0.84% | 0.84% | 0.84% | 0.84% | 0.84% |
| 0.5 | | | 1.64% | 1.18% | 3.91% | 2.45% |
| 1 | 1.00% | 0.76% | 2.45% | 1.64% | 6.26% | 4.00% |
| 2 | 1.28% | 0.85% | | | | |

TABLE III

Percent Total Related Substances as a Stability Measurement

| Time | 5° C. | | 25° C. | | 35° C. | |
|---|---|---|---|---|---|---|
| | acetate | citrate | acetate | citrate | acetate | citrate |
| 0 | 3.54% | 3.54% | 3.54% | 3.54% | 3.54% | 3.54% |
| 0.5 | | | 4.00% | 3.44% | 6.24% | 4.66% |
| 1 | 3.09% | 3.58% | 5.40% | 4.48% | 9.66% | 6.67% |
| 2 | 2.69% | 1.97% | | | | |

TABLE IV

Percent Highest Individual Impurity as a Stability Measurement

| Time | 5° C. | | 25° C. | | 35° C. | |
|---|---|---|---|---|---|---|
| | acetate | citrate | acetate | citrate | acetate | citrate |
| 0 | 0.17% | 0.17% | 0.17% | 0.17% | 0.17% | 0.17% |
| 0.5 | | | 0.50% | 0.26% | 0.60% | 0.54% |
| 1 | 0.27% | 0.40% | 0.56% | 0.28% | 0.82% | 0.61% |
| 2 | 0.29% | 0.15% | | | | |

Only the increase in the primary impurity N-desformyl vincristine is apparently affected by temperature and buffer solution. The percent of highest individual impurity is not considered to be statistically dependent on the conditions studied. In addition, the percent total impurities is proportional to the percent of the primary degradent. The conclusion to these observations is that only the measurement of the primary degradet (N-desformyl vincristine) is of importance to the stability of the solution. It shows that when the citrate buffer is used the stability of the vincristine sulfate solution is greatly increased.

Various modifications of the invention, in addition to those shown and described herein, apparent to those skilled in the art from the preceding description are considered to fall within the scope of the appended claims.

What is claimed is:

1. A pharmaceutical formulation comprising, per ml of a final solution, water, about 1 mg of vincristine sulfate, between 1 and 2 mg of a preservative selected from methyl paraben and propyl paraben either alone or in combination, and a citrate buffer at a concentration between 0.002 to about 0.01M, wherein the solution pH is between about 4.4 and 4.8.

2. A formulation according to claim 1 comprising per ml of final solution, about 1 mg of vincristine sulfate, 1.3 mg of methyl paraben, 0.2 mg of propyl paraben and a 0.005-0.01M citrate buffer, wherein the pH is between 4.5 and 4.6.

3. A pharmaceutical formulation which comprises between 0.1 to 2.5 mg/ml of a vincristine salt, between 0.0005 and 0.02M of a citrate buffer, and a preservative selected from the group consisting essentially of benzyl alcohol, phenol, m-cresol, and methyl and/or propyl paraben or mixtures thereof, wherein the pH of the solution is between 3 and 5.

4. A pharmaceutical formulation in accordance with claim 3 wherein the citrate buffer concentration is between 0.002 to 0.01M.

5. A pharmaceutical formulation in accordance with claim 3 wherein the vincristine salt is vincristine sulfate at a concentration of between 0.1 and 1.5 mg/ml.

6. A pharmaceutical formulation in accordance with claim 3 wherein the preservative comprises a mixture of methyl and propyl paraben at a total concentration of between 0.5 to 3 mg/ml.

7. A pharmaceutical formulation in accordance with claim 3 further comprising a polyol selected from the group comprising sorbitol, inositol, galactitol, xylitol, mannitol, lactose, and dextrose in a concentration between 10 and 300 mg/ml.

8. A pharmaceutical formulation in accordance with claim 3 wherein the pH is in the range of 4.4 and 4.8.

* * * * *